(12) United States Patent  (10) Patent No.: US 6,669,724 B2
Park et al.  (45) Date of Patent: Dec. 30, 2003

(54) MEDICAL STENT

(75) Inventors: Hun-Kuk Park, Kyungki-do (KR); Sung-Soon An, Seoul (KR)

(73) Assignee: M.I. Tech Co. Ltd., Kyungki-do (KR)

( * ) Notice: Subject to any disclaimer, the term of this patent is extended or adjusted under 35 U.S.C. 154(b) by 0 days.

(21) Appl. No.: 09/967,596

(22) Filed: Sep. 28, 2001

(65) Prior Publication Data

US 2002/0183828 A1 Dec. 5, 2002

(30) Foreign Application Priority Data

Jun. 5, 2001 (KR) .................................... 2001-31542

(51) Int. Cl.$^7$ .................................................. A61F 2/06
(52) U.S. Cl. ...................................................... 623/1.24
(58) Field of Search ............................ 623/1.24–1.26, 623/2.19, 2.17

(56) References Cited

U.S. PATENT DOCUMENTS

| | | | | |
|---|---|---|---|---|
| 4,510,628 A | * | 4/1985 | Kolff ........................... | 623/2.19 |
| 4,629,459 A | | 12/1986 | Ionescu et al. ................. | 623/2 |
| 5,314,473 A | | 5/1994 | Godin ........................... | 623/12 |
| 5,411,552 A | | 5/1995 | Andersen et al. ............... | 623/2 |
| 5,469,868 A | | 11/1995 | Reger ........................... | 128/898 |
| 5,500,014 A | | 3/1996 | Quijano et al. ................. | 623/3 |
| 5,824,063 A | * | 10/1998 | Cox ............................. | 623/2.1 |
| 5,855,597 A | | 1/1999 | Jayaraman ...................... | 623/1 |
| 5,861,036 A | | 1/1999 | Godin ........................... | 623/12 |
| 5,957,949 A | | 9/1999 | Leonhardt et al. .............. | 606/194 |
| 6,113,631 A | * | 9/2000 | Jansen .......................... | 623/2.17 |
| 6,162,245 A | | 12/2000 | Jayaraman ..................... | 623/1.15 |
| 6,458,153 B1 | * | 10/2002 | Bailey et al. .................. | 623/1.24 |

* cited by examiner

*Primary Examiner*—Kevin T. Truong
*Assistant Examiner*—Vy Q. Bui
(74) *Attorney, Agent, or Firm*—Blakely, Sokoloff, Taylor & Zafman

(57) ABSTRACT

A medical stent includes a first cylindrical body having a first inner diameter and a central axis, a second cylindrical body connected to one end of the first cylindrical body and having a second inner diameter, and a valve assembly for preventing food or fluid from flowing upstream. The valve assembly includes first, second and third valve members that are extended the central axis to an inner circumference wall of the first cylindrical body and spaced away from each other at an angle of 120° in a circumference direction of the first cylindrical body, the first, second and third valve members being provided with first, second and third passages, respectively, and a supporting valve member for connecting lower ends of the first, second and third valve members to an inner circumference wall of the first cylindrical body.

10 Claims, 5 Drawing Sheets

MEDICAL STENT

BACKGROUND OF THE INVENTION

1) Field of the Invention

The present invention relates to a medical stent, and more particularly, to a stent that can minimize the medical side effect by preventing regurgitation of food or fluid after the stent is disposed on an internal wall of a human body.

2) Description of the Related Art

Generally, a stent is introduced into a stricture portion of an internal wall such as a blood vessel, a bilious track, and an esophagus to enlarge the stricture portion of the internal wall and maintain the enlarged stricture portion.

Such stents are generally cylindrical-shaped and classified into an elastic type and a plastic type.

The elastic type stent is self-expandable. That is, the elastic type stent is designed to be contracted by outer force and restored to its initial shape by being self-expanded when the outer force is released. The plastic type stent is not self-expandable. That is, when outer force is applied to the plastic type, it maintains its contracted or expanded states even when the outer force is released.

Such stents are variously designed according to a portion of the internal wall where they are to be disposed. For example, when the stent is for the esophagus or the stomach, regurgitation preventing means has been provided to the stent so as to prevent food or fluid from flowing upstream, thereby preventing a serious medical side effect.

Such a stent having the regurgitation preventing means is disclosed in Korean Patent No. 170220.

The regurgitation preventing means of the Korean Patent comprises first, second and third valves mounted on an inner wall of the stent and disposed at an identical circumferential length.

However, in the stent, since each of the valves is designed to be concaved in the upper stream direction and an outer edge of each valve is integrally formed with the inner wall of the stent, the valves are easily opened when the stent is contracted and expanded by outer force. Therefore, when the stent is disposed on the internal wall of the human body in a state where it is contracted, the food or fluid may flow upstream, resulting in the serious medical side effect.

SUMMARY OF THE INVENTION

Therefore, the present invention has been made in an effort, to solve the above-described problems.

It is an objective of the present invention to provide a medical stent that can reliably prevent the regurgitation of food or fluid after the stent is disposed on an internal wall of a human body, thereby minimizing the medical side effect.

To achieve the above objective, the present invention provides a medical stent comprising:

a first cylindrical body having a first inner diameter and a central axis;

a second cylindrical body connected to one end of the first cylindrical body and having a second inner diameter; and a valve assembly for preventing food or fluid from flowing upstream, the valve assembly comprising:

first, second and third valve members that are extended from the central axis C to an inner circumference wall of the first cylindrical body and spaced away from each other at an angle of 120° in a circumference direction of the first cylindrical body, the first, second and third valve members being provided with first, second and third passages, respectively; and a supporting valve member for connecting lower ends of the first, second and third valve members to an inner circumference wall of the first cylindrical body.

Preferably, the supporting valve member is hemispherical, which is concaved toward a lower streamside.

Preferably, each of the first, second and third valve members comprises two overlapped layers between which the corresponding passage is defined when the food or fluid flows downstream, outer ends of the overlapped layers, which are proximal to the inner circumference wall of the first cylindrical body, being integrally formed with each other and inner ends of the overlapped layers, which are proximal to the central axis, being separated from each other.

Further preferably, the supporting valve member comprises first, second and third wings that are identically divided in the circumference direction on the basis of the central axis, and a circumference flange interconnecting outer edges of the first, second and third wings and attached on the inner circumference wall of the first cylindrical body. Each of the first, second and third wings connects a lower end of the adjacent overlapped layers of the adjacent valve members.

Further preferably, the first and second cylindrical bodies are covered with a cover member. The cover member is made of a material selected from the group consisting of silicon-based resin, a polyurethane-base resin, and polyethylene-based resin.

A gas exhaust passage is defined between the inner ends of the overlapped layers.

Preferably, the first inner diameter is greater than the second inner diameter, and a length of the valve assembly is identical to or greater than that of the first cylindrical body.

The medical stent may further comprise an intermediate cylindrical body between the first and second cylindrical body, the intermediate cylindrical body is formed of a material selected from the group consisting of silicon-based resin, a polyurethane-base resin, and based-based resin

BRIEF DESCRIPTION OF THE DRAWINGS

The accompanying drawings, which are incorporated in and constitute a part of the specification, illustrate an embodiment of the invention, and, together with the description, serve to explain the principles of the invention.

DETAILED DESCRIPTION OF THE PREFERRED EMBODIMENTS

A preferred embodiment of the present invention will be described in detail with reference to the accompanying drawings. In the embodiment, an elastic stent is exemplified, but the present invention is not limited to the elastic stent.

Figure 1:
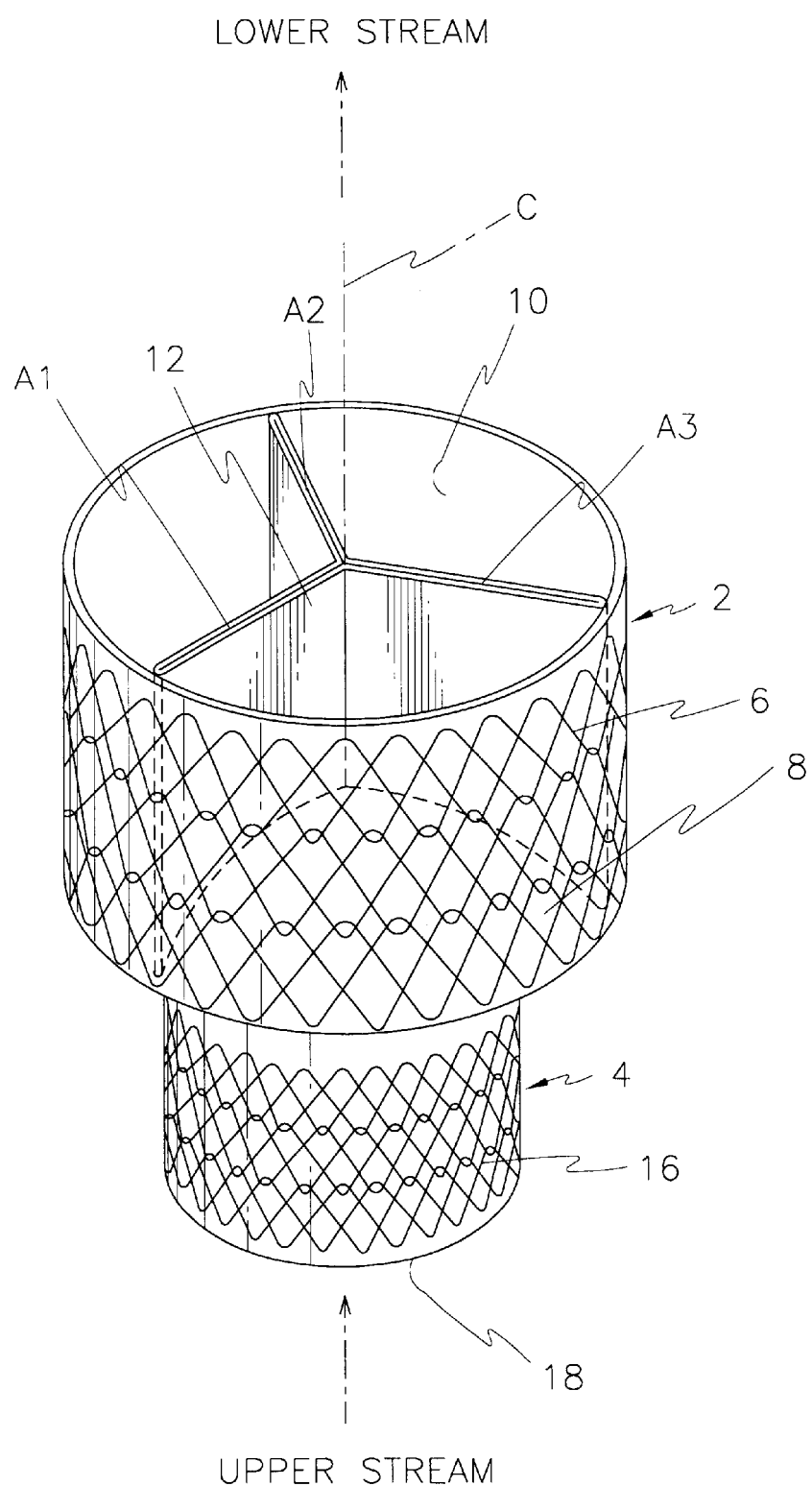
FIG. 1 is a perspective view of a medical stent according to a preferred embodiment of the present invention.
Figure 2:
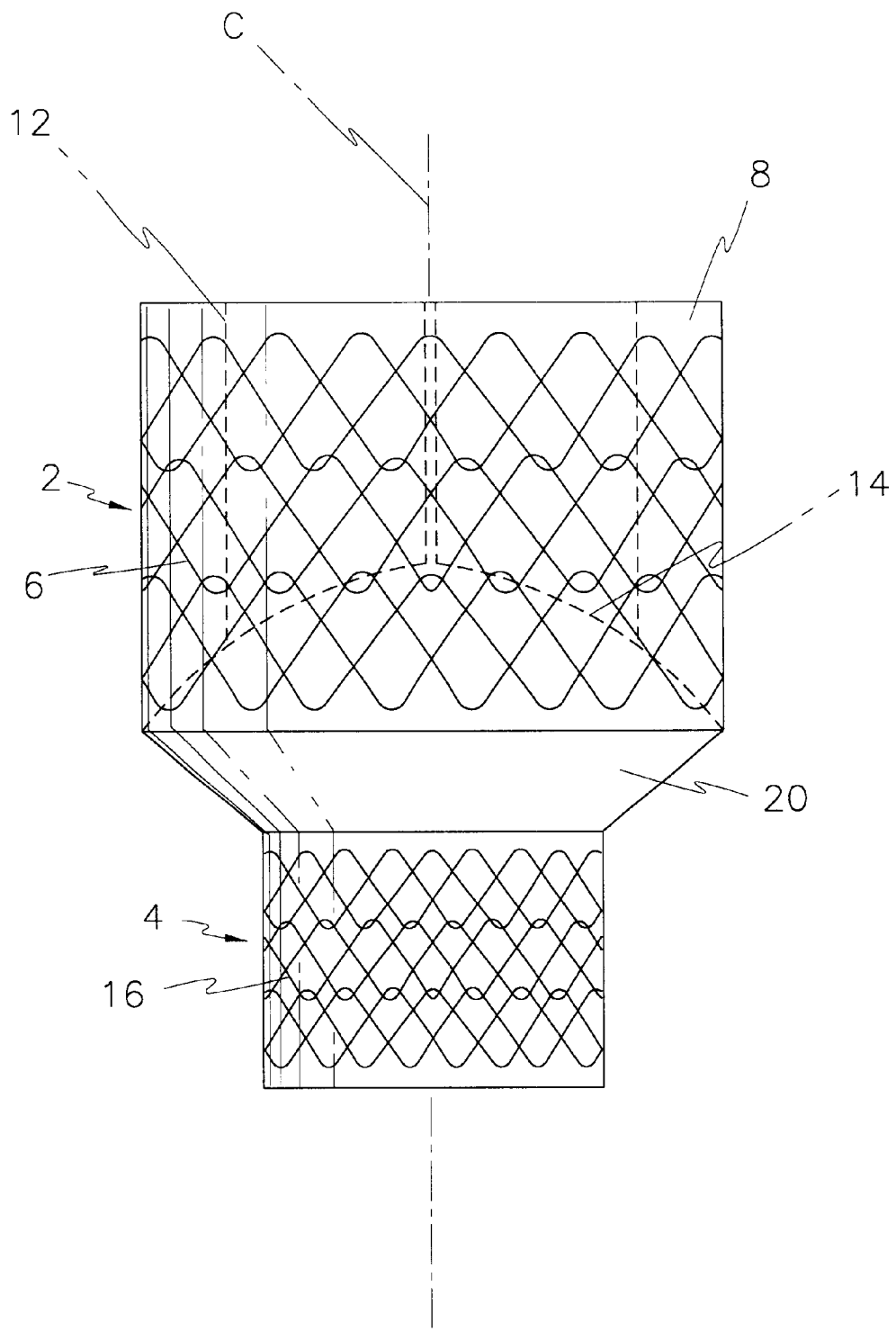
FIG. 2 is a front view of a medical stent depicted in FIG. 1.

FIGS. 1 and 2 show a medical stent according to preferred embodiment of the present invention.

The inventive medical stent comprises a first cylindrical body 2 having a first diameter and a second cylindrical body 4 integrally connected to one end of the first cylindrical body 2 and having a second diameter less than the first diameter.

The first cylindrical body 2 is located on an internal wall of a human body to enlarge a passage of the internal wall, a diameter of which is reduced by, for example, a cancer cell.

The first cylindrical body 2 comprises at least one first unit member 6 covered with a cover member 8. When more than two unit members are provided, they are connected to each other in a longitudinal direction of the stent.

The first cylindrical body 2 has a first inner diameter portion 10 through which the food and fluid move when the stent is disposed on the inner wall of the human body.

The first unit member 6 is formed of a wire bent in a zigzag shape in a circumferential direction so that the unit member 6 has a predetermined elastic force. That is, when outer force is applied to the first unit member 6, it is elastically deformed, and then when the outer force is released, it is restored to its initial shape. As the structure of the unit member 6 is well known, the detailed description thereof will be omitted herein.

The cover member 8 covers the outer and inner circumferences of the first unit member 6 so that food or fluid cannot come into the first unit member 6 through the circumferential wall of the stent. In addition, the cover member 8 prevents the metal wire from directly contacting the inner wall of the human body.

The cover member 8 is preferably made of one of silicone-based resin, polyurethane-based resin, and polyethylene-based resin. However, other materials can also be used as far as it does not harm to the human body and can be easily and elastically deformed by outer force.

Regurgitation means according to a feature of the present invention is provided in the first inner diameter portion 10. The regurgitation means functions as a valve that can prevent the food and fluid from flowing upstream.

Figure 3:
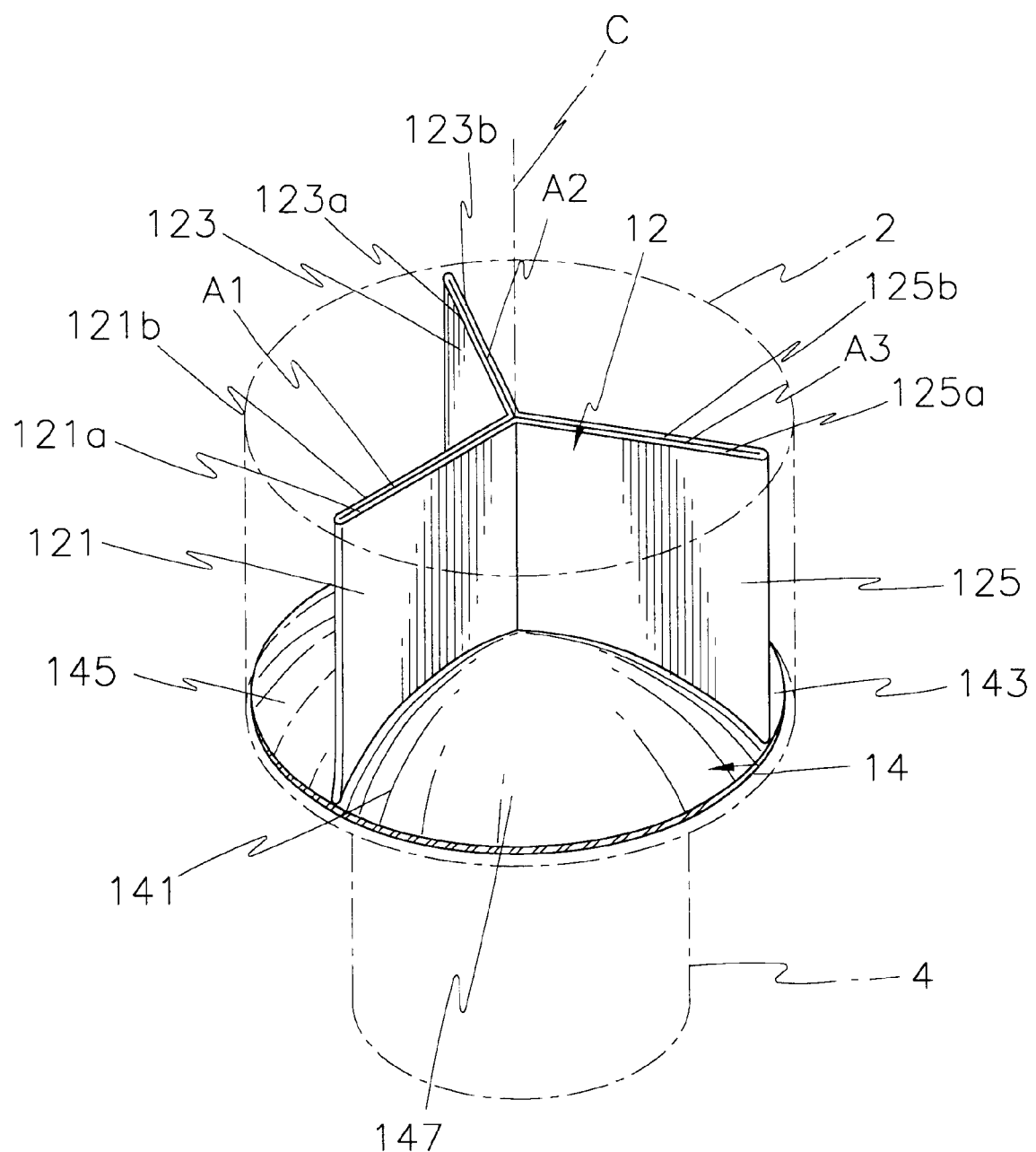
FIG. 3 is a perspective view of regurgitation preventing means depicted in FIG. 1.

The regurgitation means will be described more in detail with reference to FIGS. 3, 4 and 5. In the drawings, a lower side of the stent is an upper stream and an upper side of the stent is a lower stream.

As shown in the drawings, a valve assembly 12 is formed in the first inner diameter portion 10 of the first cylindrical body 2. The valve assembly 12 comprises first, second and third valve members 121, 123 and 125 that are extended from a central axis C of the first cylindrical body 2 to an inner circumference wall of the first cylindrical body and spaced away from each other at an angle of 120° in the circumference direction of the first cylindrical body 2 and a supporting valve member 14 for supporting the first, second and third valve members 121, 123 and 125 on the inner circumference wall of the first cylindrical body 2.

The first valve member 121 comprises two overlapped layers 121a and 121b between which a first passage A1 is defined when fluid or liquid flows downstream. Outer ends of the overlapped layers 121a and 121b, which are proximal to the inner circumference wall of the first cylindrical body 2, are integrally formed with each other to close the outer end of the first valve member 121, while the inner ends of the overlapped layers 121a and 121b, which are proximal to the central axis C, are separated from each other.

The second valve member 123 comprises two overlapped layers 123a and 123b between which a second passage A2 is defined when food or liquid flows downstream. Outer ends of the overlapped layers 123a and 123b, which are proximal to the inner circumference wall of the first cylindrical body 2, are integrally formed with each other to close the outer end of the second valve member 123, while the inner ends of the overlapped layers 123a and 123b, which are proximal to the central axis C, are separated from each other.

The third valve member 125 comprises two overlapped layers 125a and 125b between which a third passage A3 is defined food or liquid flows downstream. Outer ends of the overlapped layers 125a and 125b, which are proximal to the inner circumference wall of the first cylindrical body 2, are integrally formed with each other to close the outer end of the third valve member 125, while the inner ends of the overlapped layers 125a and 125b, which are proximal to the central axis C, are separated from each other.

The inner end of the overlapped layer 121a is integrally formed with the adjacent inner end of the overlapped layer 125a, the inner end of the overlapped layer 125b is integrally formed with the adjacent inner end of the overlapped layer 123b, and the inner end of the overlapped layer 123a is integrally formed with the inner end of the overlapped layer 121b.

The supporting valve member 14 supporting the lower ends of the first, second and third valve members 121, 123 and 125 is formed in a hemispherical-shape, which is concaved toward the downstream side. The supporting valve member 14 comprises first, second and third wings 141, 143 and 145 that are identically divided in the circumference direction on the basis of the central axis C, and a circumference flange 147 interconnecting outer edges of the first, second and third wings 141, 143 and 145 and attached on the inner circumference wall of the first cylindrical body 2.

The first wing 141 connects a lower end of the overlapped layer 121a with a lower end of the overlapped layer 125a, and the second wing 143 connects a lower end of the overlapped layer 125b with a lower end of the overlapped layer 123b, and the third wing 145 connects a lower end of the overlapped layer 123a with the overlapped layer 121b.

Accordingly, an entire shape of the supporting valve member 14 is hemispherical, while providing openings communicating with the passages A1, A2 and A3.

Such a hemispherical shape of the supporting valve member 14 allows food or fluid to be smoothly guided downstream (i.e., to a upper side in the drawing) through the first, second and third passages A1, A2 and A3 while preventing the food and fluid from flowing upstream (i.e., to the lower side in the drawing).

In addition, a central portion defined between the inner ends of the overlapped layers functions as a predetermined exhaust passage A4 (see FIG. 4) through which gas generated in the lower streamside can be smoothly exhausted through the exhaust passage A4.

The valve assembly 12 is made of a material identical to the cover member 8 such silicone-based resin, polyurethane-based resin, and polyethylene-based resin to prevent the first, second and third passages A1, A2 and A3 from being deformed irregularly when the first cylindrical body 2 is deformed by outer force.

The length of the valve assembly 12 may be identical to or greater than that of the first cylindrical body 2.

A radius R of the hemispherical supporting valve member 14 can be varied as far as it meets the purpose of the present invention.

Figure 4:
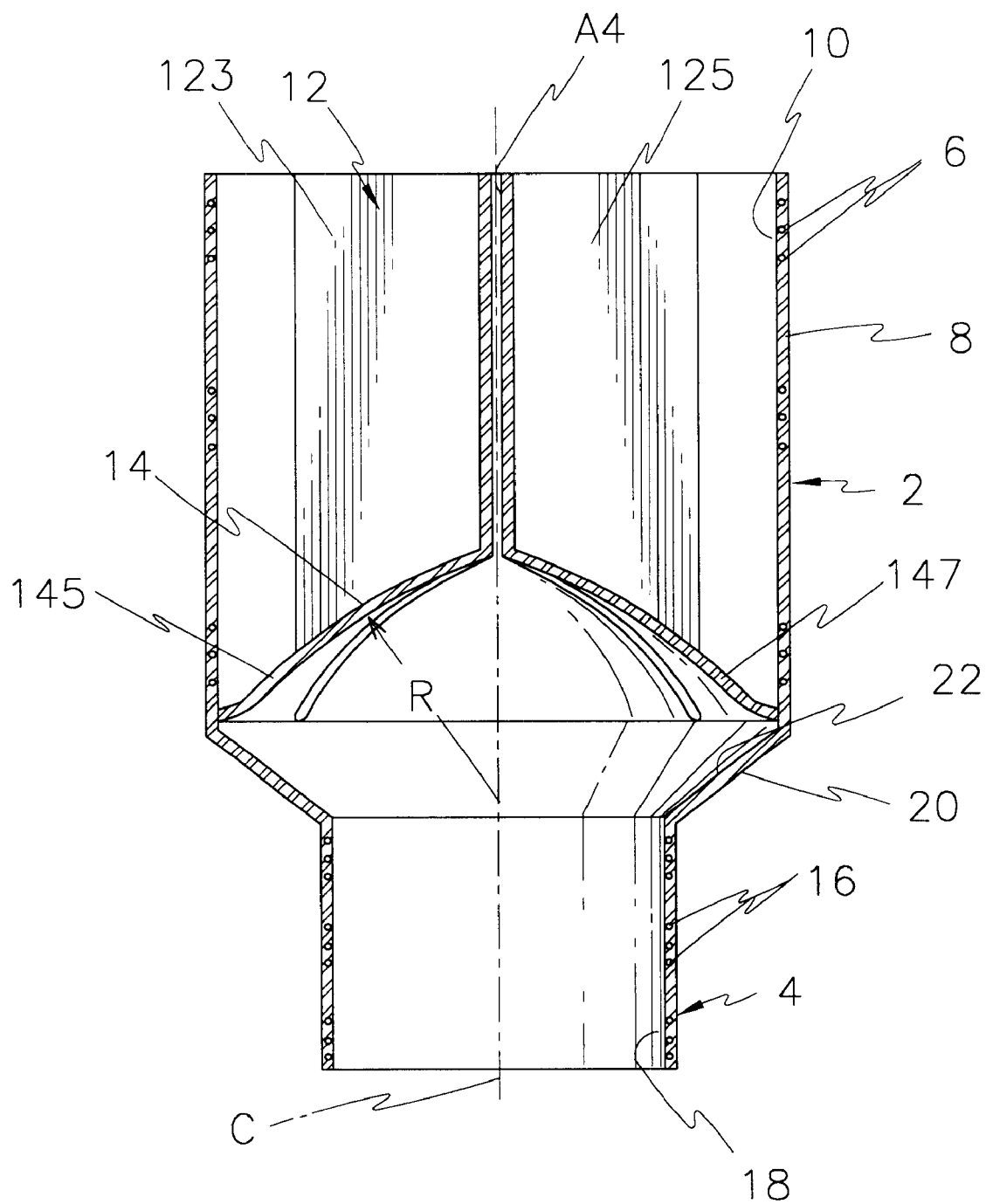
FIG. 4 is a sectional view of FIG. 1, taken in a longitudinal direction.
Figure 5:
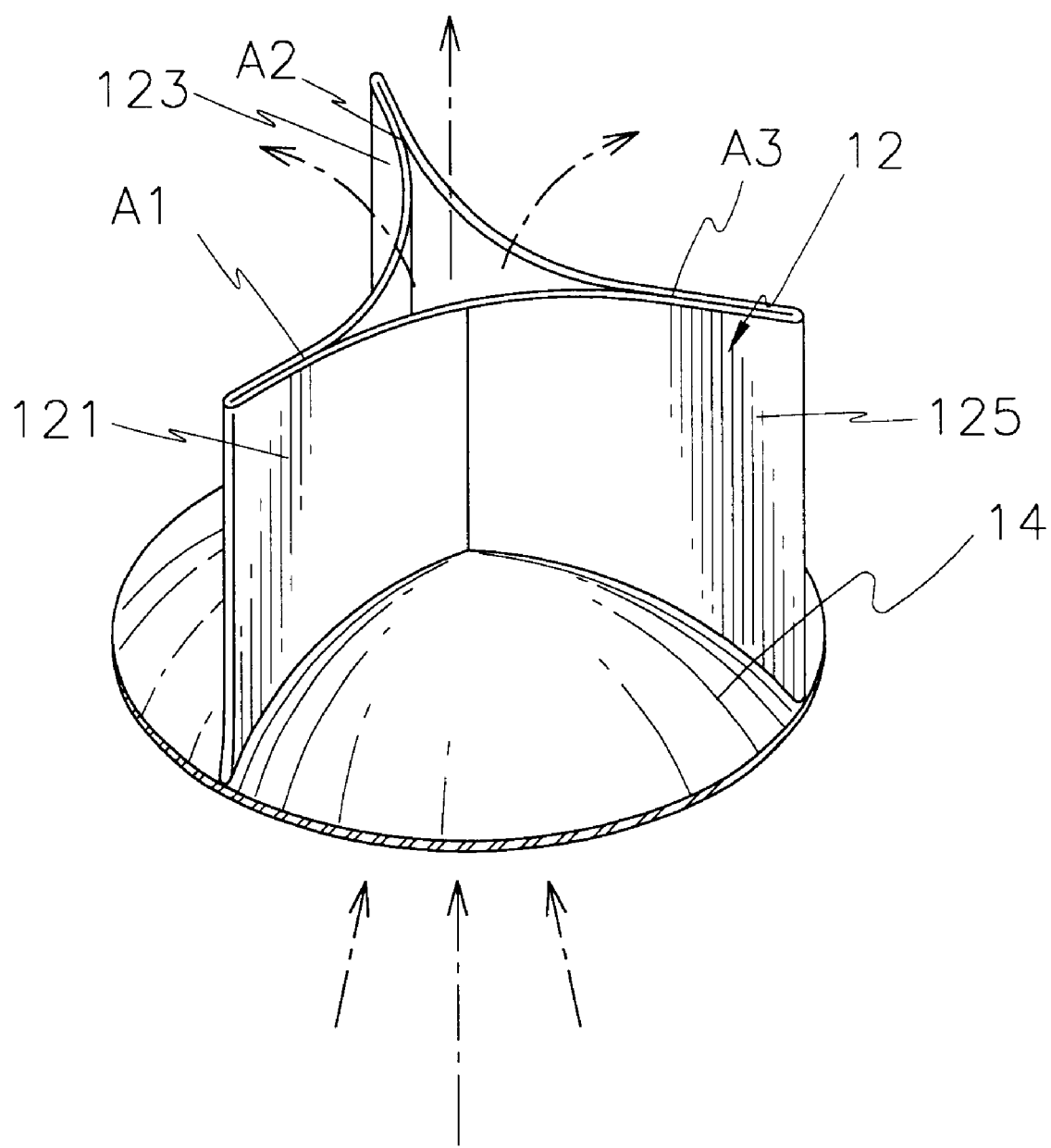
FIG. 5 is a view illustrating the operation of the regurgitation preventing means depicted in FIG. 3.

Referring to FIGS. 1 and 4, the lower end of the first cylindrical body 2 is connected to the upper end of the second cylindrical body 4 via an intermediate cylindrical body 20. The second cylindrical body 4 is disposed on the cancer cell and has an identical structure to that of the first cylindrical body 2. That is, the second cylindrical body 4 comprises at least one second unit member 16 covered with a cover member 8 and provided with a second inner diameter portion 18.

The diameter of the second cylindrical body 2 can be properly modified according to the size of the cancer cell or the location of the affected part.

The intermediate cylindrical body 20 is formed of resin without any wire unit member having elastic force and is provided with an intermediate diameter portion 22 communicating with the first diameter portion 10 of the first cylindrical body 2 with the second diameter portion 18 of the second cylindrical body 4.

As the intermediate cylindrical body does not have the unit member having the elastic force, even when the second cylindrical body 4 is deformed by outer force, the deformation force of the second cylindrical body 4 is not transmitted to the first cylindrical body 2, thereby minimizing the irregular deformation of the first, second and third passages A1, A2 and A3. As a result, regurgitation of the food and fluid in the internal wall of the human body can be effectively prevented, minimizing the medical side effect.

While this invention has been described in connection with what is presently considered to be the most practical and preferred embodiments, it is to be understood that the invention is not limited to the disclosed embodiments, but, on the contrary, is intended to cover various modifications and equivalent arrangements included within the spirit and scope of the appended claims.

What is claimed is:

1. A medical stent comprising:
    a first cylindrical body having a first diameter and a central axis, the first cylindrical body being defined by bending a wire in a zigzag-shape and covered at its inner and outer surfaces with a cover member;
    a second cylindrical body having a second diameter less than the first diameter and a second central axis identical to the central axis of the first cylindrical body, the second cylindrical body being defined by bending a wire in a zigzag-shape and covered at its inner and outer surfaces with a cover member;
    an intermediate cylindrical body for connecting the cover member of the first cylindrical body to the cover member of the second cylindrical body, the intermediate cylindrical body being formed of a material selected from the group consisting of silicone-based resin, polyurethane-based resin, and polyethylene-based resin; and
    a valve assembly for preventing fluid from being reversely flowing, the valve assembly comprising:
        first, second and third valve members formed extending from the central axis to an inner circumferential wall of the first cylindrical body and spaced away from each other at an angle of 120° in a circumferential direction on the inner circumferential wall, first, second and third valve members having first, second and third passages, respectively, and a length identical or greater than a longitudinal length of the first cylindrical body; and
        a supporting valve member for connecting the first, second and third valve members on the inner circumferential wall.

2. A medical stent of claim 1 wherein the supporting valve member is hemispherical, which is concaved toward a lower streamside.

3. A medical stent of claim 1 wherein each of the first, second and third valve members comprises two overlapped layers between which the corresponding passage is defined when the fluid flows downstream, outer ends of the overlapped layers, which are proximal to the inner circumference wall of the first cylindrical body, being integrally formed with each other and inner ends of the overlapped layers, which are proximal to the central axis, being separated from each other.

4. A medical stein of claim 3 wherein the supporting valve member comprises first, second and third wings that are identically divided in the circumference direction on the basis of the central axis, and a circumference flange interconnecting outer edges of the first second and third wings and attached on the inner circumference wall of the first cylindrical body.

5. A medical stent of claim 4 wherein each of the first, second and third wings connects a lower end of the adjacent overlapped layers of the adjacent valve members.

6. A medical stent of claim 1 wherein the first and second cylindrical bodies are covered with a cover member.

7. A medical stent of claim 6 wherein the cover member is made of a material selected from the group consisting of silicone-based resin, a polyurethane-based resin, and polyethylene-based resin.

8. A medical stent of claim 3 wherein a gas exhaust passage is defined between the inner ends of the overlapped layers.

9. A medical stent of claim 1, wherein fluid can be food.

10. A medical stent of claim 3, wherein fluid can be food.

* * * * *